(12) United States Patent
Wei et al.

(10) Patent No.: US 9,365,856 B2
(45) Date of Patent: Jun. 14, 2016

(54) METHODS OF USING A SERUM RESPONSE FACTOR ISOFORM

(71) Applicant: Board of Trustees of the University of Arkansas, Little Rock, AR (US)

(72) Inventors: Jeanne Wei, Little Rock, AR (US); Gohar Azhar, Little Rock, AR (US); Xiaomin Zhang, Little Rock, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 14/028,105

(22) Filed: Sep. 16, 2013

(65) Prior Publication Data

US 2014/0080123 A1 Mar. 20, 2014

Related U.S. Application Data

(60) Provisional application No. 61/701,219, filed on Sep. 14, 2012.

(51) Int. Cl.
*C12N 15/63* (2006.01)
*C12N 15/85* (2006.01)

(52) U.S. Cl.
CPC .............. *C12N 15/635* (2013.01); *C12N 15/85* (2013.01); *C12N 2015/8572* (2013.01)

(58) Field of Classification Search
None
See application file for complete search history.

(56) References Cited

U.S. PATENT DOCUMENTS

| | | | |
|---|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |

OTHER PUBLICATIONS

Gillet et al., The Development of Gene Therapy: From Monogenic Recessive Disorders to Complex Diseases Such as Cancer; Methods in Molecular Biology, Gene Therapy of Cancer, vol. 542; Humana Press, 2009.*

Xu et al., Drug Delivery Trends in Clinical Trials and Translational Medicine: Challenges and Opportunities in the Delivery of Nucleic Acid-Based Therapeutics; J Pharmaceutical Sciences, vol. 100, No. 1, pp. 38-52, 2011.*
Frokjaer et al., Protein drug stability: a formulation challenge; Nature Reviews: Drug Discovery; vol. 4, pp. 298-306, 2005.*
Chen et al., A review of the prospects for polymeric nanoparticle platforms in oral insulin delivery; Biomaterials, vol. 32, pp. 9826-9838, 2011.*
Esteiu-Gionnet et al., Stabilized helical peptides: overview of the gechnologies and therapeutic promises; Expert Opinion in Drug Discovery, vol. 6, No. 9, pp. 937-963, 2011.*
Chang et al., Inhibitory Cardiac Transcription Factor, SRF-N, Is Generated by Caspase 3 Cleavage in Human Heart Failure and Attenuated by Ventricular Unloading; Circulation, vol. 108, pp. 407-413, 2003.*
Johansen et al., Identification of Transcriptional Activation and Inhibitory Domains in Serum Response Factor (SRF) by Using GAL4-SRF Constructs; Mol Cell Biol. vol. 13, No. 8, pp. 4640-4647, 1993.*
Roper et al., Comparison of in vitro methods to determine drug-induced cell lethality; Cancer Res. vol. 36, pp. 2182-2188, 1976.*
Patten et al., Serum Response Factor Is Alternatively Spliced in Human Colon Cancer; Journal of Surgical Research, vol. 121, pp. 92-100, 2004.*
Agrawal et al., "Site-specific excision from RNA by RNase H and mixed-phosphate-backbone oligodeoxynucleotides", Proc. Natl. Acad. Sci. USA, 1990, pp. 1401-1405, vol. 87.
Altschul et al., "Basic Local Alignment Search Tool", J. Mol. Biol., 1990, pp. 403-410, vol. 215.
Altschul et al., "Gapped BLAST and PSI-BLAST: a new generation of protein database search programs", Nucleic Acids Research, 1997, pp. 3389-3402, vol. 25, No. 17.
Baker et al., "Effects of oligo sequence and chemistry on the efficiency of oligodeoxyribonucleotide-mediated mRNA cleavage", Nucleic Acids Research, 1990, pp. 3537-3543, vol. 18, No. 12.
Furdon et al., "RNase H cleavage of RNA hybridized to oligonucleotides containing methylphosphonate, phosphorothioate and phosphodiester bonds", Nucleic Acids Research, 1989, pp. 9193-9204, vol. 17, No. 22.
Karlin et al., "Methods for assessing the statistical significance of molecular sequence features by using general scoring schemes", Proc. Natl. Acad. Sci. USA, 1990, pp. 2264-2268, vol. 87.
Sproat et al., "Highly efficient chemical synthesis of 2'-O-methyloligoribonucleotides and tetrabiotinylated derivatives; novel probes that are resistant to degradation by RNA or DNA specific nucleases", Nucleic Acids Research, 1989, pp. 3373-3386, vol. 17, No. 9.
Walder et al., "Role of RNase H in hybrid-arrested translation by antisense oligonucleotides", Proc. Natl. Acad. Sci. USA, 1988, pp. 5011-5015, vol. 85.

* cited by examiner

*Primary Examiner* — Addison D Ault
(74) *Attorney, Agent, or Firm* — Polsinelli PC (57) ABSTRACT

The present invention encompasses methods of administering SRFΔ3. Administering SRFΔ3 may reduce proliferation of cancer cells, and modulate activity of promoters regulated by serum response factor.

6 Claims, 8 Drawing Sheets
(6 of 8 Drawing Sheet(s) Filed in Color)

SEQUENCE LISTING

```
<160> NUMBER OF SEQ ID NOS: 3

<210> SEQ ID NO 1
<211> LENGTH: 1265
<212> TYPE: DNA
<213> ORGANISM: Homo sapiens

<400> SEQUENCE: 1
atgttaccga cccaagctgg ggccgcggcg gctctgggcc ggggctcggc cctgggggc      60 agcctgaacc ggacccccgac ggggcggccg ggcggcggcg gcgggacacg cggggctaac    120
gggggccggg tccccgggaa tggcgcgggg ctcgggcccg gccgcctgga gcgggaggct    180
gcggcagcgg cggcaaccac cccggcgccc accgcggggg ccctctacag cggcagcgag    240
ggcgactcgg agtcgggcga ggaggaggag ctgggcgccg agcggcgcgg cctgaagcgg    300
agcctgagcg agatggagat cggtatggtg gtcggtgggc ccgaggcgtc ggcagcggcc    360 accggggct acgggccggt gagcggcgcg gtgagcgggg ccaagccggg taagaagacc       420
cggggccgcg tgaagatcaa gatggagttc atcgacaaca agctgcggcg ctacacgacc     480
ttcagcaaga ggaagacggg catcatgaag aaggcctatg agctgtccac gctgacaggg     540
acacaggtgc tgttgctggt ggccagtgag acaggccatg tgtataccct tgccacccga     600
aaactgcagc ccatgatcac cagtgagacc ggcaaggcac tgattcagac ctgcctcaac     660
tcgccagact ctccaccccg ttcagacccc acaacagacc agagaatgag tgccactggc     720
```

```
tttgaagaga cagatctcac ctaccaggtg tcggagtctg acagcagtgg ggagaccaag    780
gtggggcagt ggcccagcag gtcccagtgc aggccattca agtgcaccag gccccacagc    840
aagcgtctcc ctcccgtgac agcagcacag acctcacgca gacctcctcc agcgggacag    900
tgacgctgcc cgccaccatc atgacgtcat ccgtgcccac aactgtgggt ggccacatga    960
tgtaccctag cccgcatgcg gtgatgtatg cccccacctc gggcctgggt gatggcagcc   1020
tcaccgtgct gaatgccttc tcccaggcac catccaccat gcaggtgtca cacagccagg   1080
tccaggagcc aggtggcgtc ccccaggtgt tcctgacagc atcatctggg acagtgcaga   1140
tccctgtttc agcagttcag ctccaccaga tggctgtgat agggcagcag gccgggagca   1200
gcagcaacct caccgagcta caggtggtga acctggacac cgcccacagc accaagagtg   1260
aatga                                                               1265

<210> SEQ ID NO 2
<211> LENGTH: 42
<212> TYPE: DNA
<213> ORGANISM: Homo sapiens

<400> SEQUENCE: 2
ggggagacca aggtggggca gtgggcggga cagtgacgct gc                        42

<210> SEQ ID NO 3
<211> LENGTH: 11
<212> TYPE: PRT
<213> ORGANISM: Homo sapiens

<400> SEQUENCE: 3

Gly Glu Thr Lys Val Gly Gln Trp Ala Gly Gln
1               5                   10
```

METHODS OF USING A SERUM RESPONSE FACTOR ISOFORM

CROSS REFERENCE TO RELATED APPLICATIONS

This application claims the priority of U.S. provisional application No. 61/701,219, filed Sep. 14, 2012, which is hereby incorporated by reference in its entirety.

GOVERMENTAL RIGHTS

This invention was made with government support under grant number AG026091 awarded by The National Institutes of Health. The government has certain rights in the invention.

FIELD OF THE INVENTION

The invention relates to methods of using and administering serum response factor isoform SRFΔ3 to control transcription of nucleic acid sequences.

BACKGROUND OF THE INVENTION

Transcription factors are proteins that bind to specific DNA sequences, controlling the transcription of genetic information from DNA to mRNA. Transcription factors play important roles in development, intracellular signaling, and cell cycle, and therefore are of great clinical significance. Many transcription factors are either tumor suppressors or oncogenes, and thus play important roles in cancer development or prevention. Mutations in transcription factors have been associated with specific diseases.

Approximately 10% of currently prescribed drugs directly target transcription factors. Examples include tamoxifen and bicalutamide for the treatment of breast and prostate cancer, respectively, and various types of anti-inflammatory and anabolic steroids. In addition, transcription factors are often indirectly modulated by drugs through signaling cascades. However, most of these treatments are directed at the nuclear receptor class of transcription factors. Other transcription factors outside the nuclear receptor family, such as serum response factor (SRF) transcription factor, are more difficult to target with small molecule therapeutics. Therefore, there is a need for methods of targeting transcription factors that are more difficult to target with small molecule therapeutics, such as serum response factor.

SUMMARY OF THE INVENTION

One aspect of the present invention encompasses a method of reducing proliferation of a cell. The method comprises administering SRFΔ3 to the cell and performing a proliferation assay using this cell, wherein a reduced proliferation rate of the treated cell compared to an untreated cell indicates effective inhibition of proliferation.

Another aspect of the present invention encompasses a method for modulating the activity of a promoter regulated by serum response factor. The method comprises administering SRFΔ3 to a cell comprising one or more promoters regulated by serum response factor.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 8 depicts a diagram representing a network generated using GeneGo and illustrating some of the genes and pathways involved in cardiac-specific mild over-expression of wt SRF (Mild-O-SRF Tg). SRFΔ3 protein expression was decreased in the Mild-O-SRF Tg vs. Non-Tg hearts. Red thermometers indicate that the adjacent gene expression was increased and blue thermometers indicate that the gene expression was decreased in the SRF Tg vs Non-Tg. Note, in the lower half of the diagram, actin is increased whereas myosin heavy chain is decreased (a detailed legend of the symbols is provided on-line, on the Gene-Go website). At the bottom of the network, homodimers of the transcription factor SRF are depicted, binding to the CArG or serum response element of a promoter. Ternary complex factors (TCF) are attached to SRF as well as smaller SRF co-factors (pink, purple circles).

DETAILED DESCRIPTION OF THE INVENTION

SRF is a member of the MADS (MCM1, Agamous, Deficiens, and SRF) box superfamily of transcription factors. SRF is the downstream target of pathways such as the mitogen-activated protein kinase pathway (MAPK) and many immediate-early nucleic acid sequences, thereby participating in regulation of cell cycle, apoptosis, cell growth, and cell differentiation. SRF also modulates the activity of muscle-specific nucleic acid sequences. Interaction of SRF with other proteins, such as steroid hormone receptors, may contribute to regulation of muscle growth by steroids. In addition, lack of skin SRF is associated with psoriasis and other skin diseases. In humans and other mammals such as mice, the nucleic acid encoding SRF expresses a number of SRF isoforms through alternative splicing.

The human and mouse nucleic acid sequence encoding SRF comprises seven exons. Exons 1 and 2 encode the majority of the SRF binding domain, while exons 3 to exon 7 encode the transcription activation domain of the SRF protein. Four SRF isoforms resulting from alternative splicing of exons 3, 4, and 5 are known: SRFΔ5, SRFΔ45 and SRFΔ345, respectively, and the full-length counterpart (SRF-FL).

It has been discovered that a nucleic acid encoding SRF expresses a fifth isoform which lacks exon 3, SRFΔ3. As used herein, the term "SRFΔ3" refers to a SRF isoform, protein or nucleic acid encoding a protein that differs from other SRF isoforms in that exons 2 and 4 are joined, resulting in a frame shift in the translational reading frame at exon 4, a premature termination codon in exon 5, and 40 amino acid residues at the carboxy terminus unique to SRFΔ3. Also included in the definition of SRFΔ3 are functional variants, including truncations. SEQ ID NO: 1 encodes an SRFΔ3, and is "at gttacgacc caagctggg ccgcggcggc tctgggccgg ggctcggccc tgggggcag cctgaaccgg accccgacgg ggcggccggg cggcggcggc gggacacgcg gggctaacgg gggccgggtc cccgggaatg gcgcggggct cgggcccggc cgcctggagc gggaggctgc ggcagcggcg gcaaccaccc cggcgcccac cgcggggggcc ctctacagcg gcagcgaggg cgactcggag tcgggcgagg aggaggagct gggcgccgag cggcgcggcc tgaagcggag cctgagcgag atggagatcg gtatggtggt cggtgggccc gaggcgtcgg cagcggccac cggggggctac gggccggtga gcggccggt gagcggggcc aagccgggta agaagacccg gggccgcgtg aagatcaaga tggagttcat cgacaacaag ctgcggcgct acacgaccttt cagcaagagg aagacgggca tcatgaagaa ggcctatgag ctgtccacgc tgacagggac acaggtgctg ttgctggtgg ccagtgagac aggccatgtg tatacctttg ccacccgaaa actgcagccc atgatcacca gtgagaccgg caaggcactg attcagacct gcctcaactc gccagactct ccacccgtt cagacccac aacagaccag agaatgagtg ccactggctt tgaagagaca gatctcacct accaggtgtc ggagtctgac agcagtgggg agaccaag gtgggcagt ggcccagcag gtcccagtgc aggccattca agtgcaccag gccccacagc aagcgtctcc ctcccgtgac agcagcacag acctcacgca gacctcctcc agcgggacag tgacgctgcc cgccaccatc atgacgtcat ccgtgcccac aactgtgggt ggccacatga tgtacctag cccgcatgcg gtgatgtatg cccccacctc gggctgggt gatggcagcc tcaccgtgct gaatgccttc tcccaggcac catccaccat gcaggtgtca cacagccagg tcaggagcc aggtggcgtc ccccaggtgt tctgacagc atcatctggg acagtgcaga tccctgttt agcagttcag ctccaccaga tggctgtgat agggcagcag gccggagca gcagcaacct caccgagcta caggtggtga acctggacac cgcccacagc accaagagtg aatga." The sequence information of the full length human SRF mRNA sequence can be found using the GenBank accession number J03161. The newly discovered isomer of SRF is highly expressed in heart muscle cells. Methods of determining a protein sequence from a nucleic acid sequence are known in the art.

A skilled artisan will appreciate that these isoforms can be found in a variety of species. Non-limiting examples include mouse (NM_020493), rat (NM_001109302), dog (XM_845616), cat (XM_003986158), non-human primates (XM_003833266, XM_004044055, XM_002816913), cattle (NM_001206016), chicken (NM_001252141), hamster (XM_005072345), and guinea pig (XM_003473643). While the full length GenBank accession numbers are referenced, one with skill in the art would know how to make an SRFΔ3 isoform from the full length sequence. It is appreciated that the present invention is directed to analogs of SRFΔ3 in other organisms and is not limited to the mouse and human analogs. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. In some embodiments, a homolog has at least 80%, at least 81%, at least 82%, at least 83%, at least 84%, at least 85%, at least 86%, at least 87%, at least 88%, or 89% identity to SRFΔ3. In another embodiment %, a homolog has at least 90%, at least 91 at least %, at least 92 at least %, at least 93 at least %, at least 94%, at least 95%, at least 96%, at least 97%, at least 98%, at least 99%, or at least 100% identity to SRFΔ3. In yet another embodiment, SRFΔ3 may be a truncation or variant that has the same activity as the full length SRFΔ3.

Using a SRFΔ3 isoform, a method of modulating the activity of a promoter region regulated by serum response factor has been developed. Administration of SRFΔ3 was found to be capable of inhibiting cancer cell growth, and modulating activity of promoters regulated by SRF. SRFΔ3, its administration, and other components of the invention are described in further detail below.

(a) Cells

According to the invention, SRFΔ3 may be administered to a cell. In some embodiments, SRFΔ3 may be administered in vitro to a cell from a cell line. In some alternatives of the embodiments, the cell line may be a primary cell line that is not yet described. Methods of preparing a primary cell line utilize standard techniques known to individuals skilled in the art. In other alternatives, a cell line may be an established cell line. A cell line may be adherent or non-adherent, or a cell line may be grown under conditions that encourage adherent, non-adherent or organotypic growth using standard techniques known to individuals skilled in the art. A cell line may be contact inhibited or non-contact inhibited.

In some embodiments, a cell line may be an established human cell line derived from a tumor. Non-limiting examples of cell lines derived from a tumor may include the osteosarcoma cell lines 143B, CAL-72, G-292, HOS, KHOS, MG-63, Saos-2, and U-2 OS; the prostate cancer cell lines DU145, PC3 and Lncap; the breast cancer cell lines MCF-7, MDA-MB-438 and T47D; the myeloid leukemia cell line THP-1, the glioblastoma cell line U87; the neuroblastoma cell line SHSY5Y; the bone cancer cell line Saos-2; the colon cancer cell lines WiDr, COLO 320DM, HT29, DLD-1, COLO 205, COLO 201, HCT-15, SW620, LoVo, SW403, SW403, SW1116, SW1463, SW837, SW948, SW1417, GPC-16, HCT-8HCT 116, NCI-H716, NCI-H747, NCI-HSO8, NCI-H498, COLO 320HSR, SNU-C2A, LS 180, LS 174T, MOLT-4, LS513, LS1034, LS411N, Hs 675.T, CO 88BV59-1, Co88BV59H21-2, Co88BV59H21-2V67-66, 1116-NS-19-9, TA 99, AS 33, TS 106, Caco-2, HT-29, SK-CO-1, SNU-C2B and SW480; and the pancreatic carcinoma cell line Panc1. In an exemplary embodiment, a cell contacted by a composition of the invention is derived from the colon cancer cell line HT29. In another exemplary embodiment, a cell contacted by a composition of the invention is derived from the colon cancer cell line SW480.

In other embodiments, a cell line may be an established myogenic cell line derived from muscle tissue. Non-limiting examples of myogenic cell lines may include the mouse C2C12 myoblast cell line and the mouse Sol8 cell line.

In yet other embodiments, a cell line may be an established cardiogenic cell line derived from heart tissue. Non-limiting examples of cardiogenic cell lines may include the H9C2 cell line and the HL-1 mouse cardiac cell line.

In other embodiments, a cell line may be an established cell line routinely used in the lab, such as the HeLa cell line and the NIH3T3 cell line.

In some embodiments, SRFΔ3 may be administered to reduce proliferation of a cell from a cell line. In some embodiments, administration of SRFΔ3 may reduce proliferation of a cell from a cell line to about 90% to about 20% of the proliferation rate of an untreated cell. In other embodiments, administration of SRFΔ3 may reduce proliferation of a cell from a cell line to about 80% to about 40% of the proliferation rate of an untreated cell. In still other embodiments, administration of SRFΔ3 may reduce proliferation of a cell from a cell line to about 60% to about 20% of the proliferation rate of an untreated cell. In yet other embodiments, administration of SRFΔ3 may reduce proliferation of a cell from a cell line to about 90%, about 85%, about 80%, about 75%, about 70%, about 65%, about 60%, about 55%, about 50%, about 45%, about 40%, about 35%, about 30%, about 25% or about 20% of the proliferation rate of an untreated cell. In each of the above embodiments, the cell line may or may not be a cancerous cell line.

In other embodiments, SRF may be administered in vivo to a cell in a subject. A subject may be a rodent, a human, a livestock animal, a companion animal, or a zoological animal. In one embodiment, a subject may be a rodent, e.g. a mouse, a rat, a guinea pig, etc. In another embodiment, a subject may be a livestock animal. Non-limiting examples of suitable livestock animals may include pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In preferred embodiments, a subject is a mouse. In exemplary embodiments, a subject is a human.

(b) Modulating Promoter Activity

In some aspects of the invention, SRFΔ3 may be administered to modulate promoter activity. The term promoter, as used herein, may mean a synthetic or naturally-derived molecule which is capable of conferring or activating expression of a nucleic acid in a cell. SRF isoforms regulate transcription of target nucleic acid sequences by binding to serum response elements (SREs) in the promoter regions of target nucleic acid sequences. As such, administration of SRFΔ3 may modulate the transcription of any nucleic acid sequence operably linked to a promoter comprising a SRE. A promoter region of target nucleic acid sequences may comprise one or more than one SRE. For instance a promoter region of target nucleic acid sequences may comprise one, two, three, four, five or more SREs.

Nucleic acid sequences operably linked to a promoter modulated by SRFΔ3 administration may encode a polypeptide, or the nucleic acid sequences may encode untranslated ribonucleic acid (RNA) sequences such as transfer RNA, ribosomal RNA, and microRNA sequences. In some embodiments, SRFΔ3 may be administered to modulate promoter activity of nucleic acid sequences encoding a polypeptide. In other embodiments, SRFΔ3 may be administered to modulate promoter activity of nucleic acid sequences encoding an untranslated ribonucleic acid sequence.

SRFΔ3 may be administered to modulate promoter activity of nucleic acid sequences normally associated with a promoter comprising a SRE, or may be administered to modulate promoter activity of a heterologous nucleic acid sequence. In some embodiments, SRFΔ3 may be administered to modulate promoter activity of nucleic acid sequences normally associated with the promoter comprising a SRE. Non-limiting examples of nucleic acid sequences normally associated with a promoter comprising a SRE may include nucleic acid sequences encoding the sarco/endoplasmic reticulum $Ca^{2+}$-ATPase protein (SERCA) polypeptide, the early growth response protein 1 (EGR-1), immediate-early nucleic acid sequences such as the nucleic acid sequence encoding c-fos protein, the nuclear transcription factor Y subunit alpha polypeptide, the Src proto-oncogene tyrosine-protein kinase polypeptide, the CREB-binding protein, general transcription factor II-I protein, the activating transcription factor 6 protein, Nuclear receptor co-repressor 2 protein, CCAAT/enhancer-binding protein beta protein, the GATA4 transcription factor, the myogenin protein, the general transcription factor IIF subunit 1, the transcriptional enhancer factor TEF-1 protein, the ETS domain-containing protein Elk-4, the promyelocytic leukemia protein, and the activating signal cointegrator 1 complex subunit protein.

In one embodiment, a nucleic acid sequence operably linked to a promoter comprising a SRE is a nucleic acid sequence encoding the sarco/endoplasmic reticulum $Ca^{2+}$-ATPase protein polypeptide SERCA2. SERCA2 has been implicated in Darier's disease; Brody's disease; a cardiomyopathy such as hypertrophy, heart failure, fatal arrhythmia, congestive heart failure; cancer such as colon cancer, gastric cancer, prostate cancer, liver cancer; primary skeletal muscle myopathy such as muscular dystrophy, myotonia, neuromyotonia, nemaline myopathy, multi/minicore myopathy, centronuclear myopathy, myotubular myopathym, mitochondrial myopathies, familial periodic paralysis, inflammatory myopathies, metabolic myopathies, glycogen storage diseases, lipid storage disorder, drug-induced myopathy, glucocorticoid myopathy, alcoholic myopathy, dermatomyositis, polymyositis, inclusion body myositis, myositis ossificans, rhabdomyolysis, and myoglobinurias; or primary skeletal muscle atrophy such as primary skeletal muscle atrophy which may result from cancer, AIDS, congestive heart failure, COPD (chronic obstructive pulmonary disease), renal failure, severe burns, old age, and cachexia.

In another embodiment, a nucleic acid sequence operably linked to a promoter comprising a SRE is a nucleic acid sequence encoding the early growth response protein 1 (EGR-1). EGR-1 is an important immediate early gene with rapid activation following stress, associated with increases in inflammatory cytokines and procoagulants. EGR-1 has been implicated in prostate cancer, breast cancer, lung cancer, and connective tissue diseases (fibrotic diseases) such as scleroderma and schizophrenia and pathological fibrosis after myocardial infarction and tissue damage in various organs following ischemia or inflammatory injury.

In some embodiments, SRFΔ3 may be administered to modulate the activity of a promoter comprising a SRE wherein the promoter is operably linked to a heterologous nucleic acid sequence. In one embodiment, a heterologous nucleic acid sequence may encode a reporter. As used herein, a reporter refers to a biomolecule that may be used as an indicator of transcription through a particular promoter. Suitable reporters are known in the art. Non-limiting examples of reporters may include visual reporters or selectable-marker reporters. Visual reporters typically result in a visual signal, such as a color change in the cell, or fluorescence or luminescence of the cell. For instance, the reporter LacZ, which encodes β-galactosidase, will turn a cell blue in the presence of a suitable substrate, such as X-gal. Alternatively, a fluorescent protein may be used, such as GFP, yellow fluorescent protein (e.g. YFP, Citrine, Venus, YPet), blue fluorescent protein (e.g. EBFP, EBFP2, Azurite, mKalama1), cyan fluorescent protein (e.g. ECFP, Cerulean, CyPet), or other suitable fluorescent protein. Additionally, luciferase may be used. Selectable-marker reporters typically confer a selectable trait to the cell, such as drug resistance (e.g. antibiotic resistance). In a preferred embodiment, the heterologous nucleic acid sequence of the invention encodes luciferase.

In some embodiments, SRFΔ3 may be administered to modulate the activity of a promoter normally associated with a nucleic acid sequence encoding SERCA2, wherein the promoter is operably linked to a heterologous nucleic acid sequence encoding luciferase. Administration of SRFΔ3 may increase or reduce expression of a heterologous nucleic acid sequence encoding luciferase. In one embodiment, administration of SRFΔ3 may reduce expression of the heterologous nucleic acid sequence encoding luciferase. In a preferred embodiment, administration of SRFΔ3 may increase expression of a heterologous nucleic acid sequence encoding luciferase. Administration of SRFΔ3 may increase expression of a heterologous nucleic acid sequence encoding luciferase by about 2 to about 5 fold compared to expression of a heterologous nucleic acid sequence encoding luciferase when SRFΔ3 is not administered. In some embodiments, administration of SRFΔ3 may increase expression of a heterologous nucleic acid sequence encoding luciferase by about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8. 2.9, about 3, about 3.1, about 3.2, about 3.3, about 3.4, about 3.5, about 3.6, about 3.7, about 3.8, about 3.9, about 4, about 4.1, about 4.2, about 4.3, about 4.5, about 4.6, about 4.7, about 4.8, about 4.9, or about 5 fold compared to expression of a heterologous nucleic acid sequence encoding luciferase when SRFΔ3 is not administered. In preferred embodiments, administration of SRFΔ3 may increase expression of a heterologous nucleic acid sequence encoding luciferase by about 2.5 to about 3.5 fold compared to expression of a heterologous nucleic acid sequence encoding luciferase when SRFΔ3 is not administered.

In other embodiments, SRFΔ3 may be administered to modulate the activity of a promoter normally associated with a nucleic acid sequence encoding EGR-1, wherein the promoter is operably linked to a heterologous nucleic acid sequence encoding luciferase. Administration of SRFΔ3 may increase or reduce expression of a heterologous nucleic acid sequence encoding luciferase. In one embodiment, administration of SRFΔ3 may increase expression of a heterologous nucleic acid sequence encoding luciferase. In a preferred embodiment, administration of SRFΔ3 may reduce expression of a heterologous nucleic acid sequence encoding luciferase. Administration of SRFΔ3 may reduce expression of a heterologous nucleic acid sequence encoding luciferase by about 2 to about 5 fold compared to expression of a heterologous nucleic acid sequence encoding luciferase when SRFΔ3 is not administered. In some embodiments, administration of SRFΔ3 may reduce expression of the heterologous nucleic acid sequence encoding luciferase by about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.5, about 4.6, about 4.7, about 4.8, about 4.9, or about 5 fold compared to expression of a heterologous nucleic acid sequence encoding luciferase when SRFΔ3 is not administered. In preferred embodiments, administration of SRFΔ3 may reduce expression of a heterologous nucleic acid sequence encoding luciferase by about 2.5 to about 3.5 fold compared to expression of a heterologous nucleic acid sequence encoding luciferase when SRFΔ3 is not administered.

(c) Inhibiting Proliferation of a Cancer Cell

In other aspects of the invention, SRFΔ3 may be administered to inhibit proliferation of a cancer cell. The cancer cell may be a primary or metastatic cancer cell at early stage or late stage of development. Non-limiting examples of neoplasms or cancer cells that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

(d) Administration

According to the invention, exogenous SRFΔ3 may be administered to a cell. As used herein, exogenous is defined as not the natural form of SRFΔ3 found in the cell. As used herein, the term "administering SRFΔ3" may refer to any method that may lead to increasing the level of SRFΔ3 protein in a cell. Non-limiting examples of methods of administering SRFΔ3 to a cell may include introducing the SRFΔ3 protein into the cell, introducing a nucleic acid sequence capable of expressing the SRFΔ3 protein into the cell, enhancing the stability of the ribonucleic acid sequence encoding the SRFΔ3 protein in the cell, and altering alternative splicing of the ribonucleic acid sequence encoding SRF to generate nuclei acid sequences encoding the SRFΔ3 isoform of SRF.

In each of the below embodiments, the amount (or dose) of SRFΔ3 can and will vary depending on variables such as the method of administration (i.e. whether SRFΔ3 is administered as a protein, as a nucleic acid construct capabale of expressing SRFΔ3 protein, etc.), the intended cell or tissue, or the intended effect of administration of SRFΔ3 protein, as will be appreciated by one of skill in the art. In an exemplary embodiment, the dose that provides the greatest therapeutic benefit to the subject is generally used.

i. Protein Transfection.

In some embodiments, the SRFΔ3 protein may be administered to a cell. Methods of administering a protein to a cell are known in the art. For instance, the SRFΔ3 protein may be administering to a cell by injection, using a cell or vesicle, or by transfection into the cell via a protein transfection agent. In one embodiment, the SRFΔ3 protein may be administered to a cell by injection into the cell. In another embodiment, the SRFΔ3 protein may be administered to a cell using a vesicle. Vesicles may be as described further below. In yet another embodiment, the SRFΔ3 protein may be administered to a cell via a protein transfection agent. Non-limiting examples of protein transfection agents may include the Influx® pinocytic cell-loading agent, the BIOPORTER® transfection agent, the Pierce protein transfection reagent, the TransPass P Protein Transfection Reagent, the Chariot Protein Delivery Reagent, the ProteoJuice™ Protein Transfection Reagent, the Xfect Protein Transfection Reagent, the Lipodin-Pro™ Protein Transfection Reagent, BioPORTER® Protein Delivery Reagent, PULSIN™.

The protein may be purified before administration to a cell. Methods of purifying proteins are generally known in the art of protein biochemistry. For example, the polypeptides may be purified via standard methods including electrophoretic, molecular, immunological and chromatographic techniques, ion exchange, hydrophobic, affinity, and reverse-phase HPLC chromatography, and chromatofocusing. As another example, the polypeptide may be purified from the flow through of reverse-phase beads. Ultrafiltration and diafiltration techniques, in conjunction with protein concentration may also be used. For general guidance in suitable purification techniques, see Scopes, R., Protein Purification, Springer-Vertag, NY (1982).

ii. Transfection of Nucleic Acid expressing SRFΔ3.

In some embodiments, SRFΔ3 protein may be administered to a cell by introducing into the cell a nucleic acid sequence capable of expressing SRFΔ3 protein. In short, an expression construct may be constructed that generates SRFΔ3 protein when expressed in a cell after being introduced into the cell. A promoter may regulate the expression of a nucleic acid sequence constitutively or differentially with respect to a cell, a tissue or an organ in which expression occurs or, with respect to the developmental stage at which expression occurs, or in response to external stimuli such as physiological stresses, pathogens, metal ions, or inducing agents or activators (i.e. an inducible promoter).

Methods of making an expression construct are known in the art. In brief, a nucleic acid sequence encoding SRFΔ3 protein is operably linked to a promoter. The term promoter, as used herein, may mean a synthetic or naturally-derived molecule which is capable of conferring or activating expression of a nucleic acid sequence in a cell. The promoter may be a promoter normally associated with a nucleic acid sequence encoding SRF, or may be a heterologous promoter. A heterologous promoter may be derived from such sources as viruses, bacteria, fungi, plants, insects, and animals.

A promoter may be constitutive or inducible. Non-limiting examples of inducible promoters may include promoters induced by the presence of a small molecule (e.g., IPTG, galactose, tetracycline, steroid hormone, abscisic acid), a metal (e.g., copper, zinc, cadmium), an environmental factor (e.g., heat, cold, stress), and the expression of an exogenous protein (e.g., T7 RNA polymerase, SP6 RNA polymerase). Non-limiting examples of a constitutive promoter may include beta-actin promoter, cytomegalovirus intermediate-early (CMV) promoter, Rous sarcoma virus (RSV) promoter, simian virus 40 early (SV40) promoter, ubiquitin C promoter, elongation factor 1 alpha (EF1α) promoter, a promoter comprising the tetracycline response element (TRE) nucleic acid sequence, and the CMV IE promoter, and combinations thereof.

In some embodiments, the expression system may further comprise a transcription termination sequence. A transcription termination sequence may be included to prevent inappropriate expression of nucleic acid sequences adjacent to the heterologous nucleic acid sequence.

All the nucleic acid sequences of the invention may be obtained using a variety of different techniques known in the art. The nucleotide sequences, as well as homologous sequences, may be isolated using standard techniques, purchased or obtained from a depository. Once the nucleotide sequence is obtained, it may be amplified for use in a variety of applications, using methods known in the art.

In some embodiments, the expression system is incorporated into a vector. One of skill in the art would be able to construct a vector through standard recombinant techniques (see, for example, Sambrook et al., 2001 and Ausubel et al., 1996, both incorporated herein by reference). Vectors include but are not limited to, plasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

The nucleic acid encoding the SRFΔ3 protein may also be operably linked to a nucleotide sequence encoding a selectable marker. The selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of selectable markers that confer antibiotic resistance include, but are not limited to, puromycin resistance gene (pac), neomycin resistance gene, hygromycin resistance gene, phlebomycin resistance gene, and blasticidin resistance gene. These genes encode for proteins that impart resistance to antibiotics such as puromycin, geneticin (G418), hygromycin, zeocin, and blasticidin, respectively. In a preferred embodiment, the operably linked antibiotic resistance gene may be pac, which encodes resistance to puromycin.

The expression construct encoding the SRFΔ3 protein may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. The exogenous nucleic acid that is introduced to the cell may be linear or circular, may be single-stranded or double-stranded, and may be DNA, RNA, or any modification or combination thereof.

The expression construct encoding the SRFΔ3 protein may be introduced into the cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect. Nanoparticles may be as described further below.

Upon introduction into the cell, the expression construct encoding the SRFΔ3 protein may be integrated into a chromosome. In some embodiments, integration of the expression construct encoding the SRFΔ3 protein into a cellular chromosome may be achieved with a mobile element. The mobile element may be a transposon or a retroelement. A variety of transposons are suitable for use in the invention. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use in the invention and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include L1 from mammals and R2Bm from silkworm.

Integration of the exogenous nucleic acid into a cellular chromosome may also be mediated by a virus. Viruses that integrate nucleic acids into a chromosome include adeno-associated viruses and retroviruses. Adeno-associated virus (AAV) vectors may be from human or nonhuman primate AAV serotypes and variants thereof. Suitable adeno-associated viruses include AAV type 1, AAV type 2, AAV type 3, AAV type 4, AAV type 5, AAV type 6, AAV type 7, AAV type 8, AAV type 9, AAV type 10, and AAV type 11. A variety of retroviruses are suitable for use in the invention. Retroviral vectors may either be replication-competent or replication-defective. The retroviral vector may be an alpharetrovirus, a betaretrovirus, a gammaretrovirus, a deltaretrovirus, an epsilonretrovirus, a lentivirus, or a spumaretrovirus. In a preferred embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV). In an exemplary embodiment, the lentiviral vector may be an HIV-derived vector.

Integration of the expression construct encoding the SRFΔ3 protein into a chromosome of the cell may be random. Alternatively, integration of the expression construct encoding the SRFΔ3 protein may be targeted to a particular sequence or location of a chromosome. In general, the general environment at the site of integration may affect whether the integrated expression construct encoding the SRFΔ3 protein is expressed, as well as its level of expression.

Cells transfected with the expression construct encoding the SRFΔ3 protein generally will be grown under selection to isolate and expand cells in which the nucleic acid has integrated into a chromosome. Cells in which the expression construct encoding the SRFΔ3 protein has been chromosomally integrated may be maintained by continuous selection with the selectable marker as described above. The presence and maintenance of the integrated exogenous nucleic acid sequence may be verified using standard techniques known to persons skilled in the art such as Southern blots, amplification of specific nucleic acid sequences using the polymerase chain reaction (PCR), and/or nucleotide sequencing.

iii. Enhance Stability of the RNA.

The mRNA encoding SRFΔ3 contains a premature termination codon (PTC), which is a target of nonsense-mediated mRNA decay (NMD), resulting in decreased levels of SRFΔ3 protein. Nonsense-mediated mRNA decay is a surveillance mechanism that minimizes the translation and regulates the stability of RNAs that contain chain termination nonsense mutations. mRNA molecules comprising nonsense mutations are detected by the splicing machinery and transported out of the nucleus and into the cytosol where the RNA is degraded. Stated another way, the level of mRNA encoding SRFΔ3 is reduced due to the premature termination codon in the mRNA encoding SRFΔ3, leading to reduced levels of expression of SRFΔ3. As such, the SRFΔ3 protein may be administered to a cell by inhibiting NMD. Inhibiting NMD may lead to increased stability and translation of the mRNA encoding SRFΔ3, and may result in increasing the level of SRFΔ3 protein in a cell. Methods of inhibiting NMD in a cell are known in the art. For instance, NMD may be inhibited by nonsense suppression which promotes read-through of eukaryotic stop codons by ribosomes. Non-limiting examples of compounds that may be used to promote read-through of eukaryotic stop codons may be aminoglycoside antibiotics, gentamicin sulfate, Acetylamino benzoic acid compounds, nucleoside compounds, 1,2,4-oxadiazole benzoic acid compounds, compounds that inhibit ribosomal proteins such as eIF5A, and clitocine and compounds related to clitocine.

iv. Alter Splicing.

In some embodiments, the SRFΔ3 protein may be administered to a cell by altering the splicing of the nucleic acid sequence encoding SRF to generate a nucleic acid sequence encoding SRFΔ3. Methods of altering splicing of an mRNA in a cell are known in the art. For instance, the mRNA splicing may be altered by administering an antisense oligonucleotide. An antisense oligonucleotide is a single stranded ribonucleic acid or deoxyribonucleic acid complementary to a chosen sequence. Antisense oligonucleotides may target a specific, complementary, coding or non-coding, nucleic acid. Depending on the antisense oligonucleotide used, the binding of the oligonucleotide to its target nucleic acid sequence may or may not activate RNAse H. In some embodiments, the antisense oligonucleotide activates RNAse H, which degrades the target nucleic acid. In preferred embodiments, the antisense oligonucleotide does not activate RNAse H. In an exemplary embodiment, the antisense oligonucleotide of the invention is complementary to the nucleic acid sequence encoding SRF, does not activate RNAse H, and alters the splicing of the nucleic acid encoding SRF to generate an mRNA encoding SRFΔ3.

Methods of making antisense oligonucleotides which do not activate RNase H are known in the art. See, e.g., U.S. Pat. No. 5,149,797 incorporated herein by reference. Such antisense oligonucleotides may contain one or more structural modification which sterically hinders or prevents binding of RNase H to a duplex molecule comprising the oligonucleotide, but does not substantially hinder or disrupt duplex formation. Antisense oligonucleotides that do not activate RNAse H may include oligonucleotides wherein at least one, two or more of the internucleotide bridging phosphate residues are modified phosphates, such as methyl phosphonates, methyl phosphonothioates, phosphoromorpholidates, phosphoropiperazidates and phosphoramidates. For instance, every other one of the internucleotide bridging phosphate residues may be a modified phosphate, contain a 2' loweralkyl moiety (e.g., C1-C4, linear or branched, saturated or unsaturated alkyl, such as methyl, ethyl, ethenyl, propyl, 1-propenyl, 2-propenyl, and isopropyl) or a combination thereof. In some embodiments, the antisense oligonucleotide of the invention that does not activate RNAse H, and disrupts the splicing of the nucleic acid encoding SRF to generate an mRNA encoding SRFΔ3 is a 2'-O-(2-methoxyethyl) (MOE)-modified antisense oligonucleotide.

Other methods of modifying an oligonucleotide to hinder binding of RNAse H may be found in P. Furdon et al., Nucleic Acids Res. 17, 9193-9204 (1989); S. Agrawal et al., Proc. Natl. Acad. Sci. USA 87, 1401-1405 (1990); C. Baker et al., Nucleic Acids Res. 18, 3537-3543 (1990); B. Sproat et al., Nucleic Acids Res. 17, 3373-3386 (1989); R. Walder and J. Walder, Proc. Natl. Acad. Sci. USA 85, 5011-5015 (1988) the disclosures of all of which are incorporated herein, in their entirety, by reference.

The antisense oligonucleotide of the invention may be a deoxyribonucleotide oligonucleotide or a ribonucleotide oligonucleotide. The antisense oligonucleotide may be any length provided it binds selectively to the intended location. In general, the antisense oligonucleotide may be from 8, 10 or 12 nucleotides in length up to 20, 30, or 50 nucleotides in length.

The term "antisense oligonucleotide" includes the physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, NH4+, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

v. In Vivo Administration

In some embodiments, SRFΔ3 protein may be administered to a cell in vitro. In other embodiments, SRFΔ3 protein may be administered to a cell in vivo. Methods of formulating and administering a compound to a cell in vivo are known in the art.

For instance, a composition comprising SRFΔ3 protein may generally be administered parenteraly, intraperitoneally, intravascularly, or intrapulmonarily in dosage unit formulations containing conventional nontoxic pharmaceutically acceptable carriers, adjuvants, and vehicles as desired. The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

vi. Administration Using Nanoparticles

Any of the methods of administering SRFΔ3 protein described above may be administered using a vehicle for cellular delivery. In these embodiments, typically a composition comprising SRFΔ3 is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the composition of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the composition of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parantheses) n-dodecanoate(laurate), n-tretradecanoate(myristate), n-hexadecanoate(palmitate), n-octadecanoate(stearate), n-eicosanoate(arachidate), n-docosanoate(behenate), n-tetracosanoate(lignocerate), cis-9-hexadecenoate(palmitoleate), cis-9-octadecanoate(oleate), cis,cis-9,12-octadecandienoate(linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stabilty of activity properties. The above mentioned phosphoplipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the composition of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concetration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional goups at their surface. For example, hydrophilic end groups, such as carboxyl groups, would typically make a water-soluble dendrimer. Alternatively, phospholipids may be incorporated in the suraface of an dendrimer to facilitate absorption across the skin. Any of the phospholipids detailed for use in liposome embodiments are suitable for use in dendrimer embodiments. Any method generally known in the art may be utiized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

vii. Targeting

In some embodiments, a composition of the invention may also be targeted to a particular cell or cell type. For instance, a composition of the invention may be targeted to a tumor cell or to a muscle cell. A targeted composition may comprise a targeting moiety. A targeting moiety directs or targets the composition and its attached nucleic acid cargo to a particular site or location. Targeted compositions may comprise a wide variety of targeting moieties conjugated to the outer surface of the composition, including but not limited to antibodies, antibody fragments, peptides, small molecules, polysaccharides, nucleic acids, aptamers, growth factors (such as EGF), folates, peptidomimetics, other mimetics or drugs alone or in combination. These targeting moieties may be utilized to specifically direct the composition to cellular epitopes and/or receptors. The targeting moieties may be conjugated directly or indirectly to the composition. Targeting moieties may be chemically attached to the surface of nanoparticles by a variety of methods depending upon the nature of the targeting moiety and composition of the nanoparticle surface.

EXAMPLES

The following examples illustrate various iterations of the invention.

Example 1

Identification of Novel SRF Splicing Isoforms

Hundreds of cDNA clones were analyzed and sequenced. In short, heart cDNA samples (Clontech) were pooled from 10 male/female humans, ages 21-51, who died from trauma, 14 spontaneously aborted male/female human fetuses, ages 20-25 weeks, and autopsy samples from elderly humans, ages 72, 102, and 104 years. Skeletal muscle cDNA samples were from a 24 year old and from a 91 year old human. Approximately 200 plasmid constructs containing all the potential SRF isoforms from human and mouse cardiac and skeletal tissue were examined. The pGEM-T plasmid constructs containing all the potential SRF isoforms were digested with both NcoI and NotI restriction enzymes, and then separated by electrophoresis in a 1.2% agarose gel. The plasmids containing a PCR insert were then subjected to sequence analysis.

Figure 1:
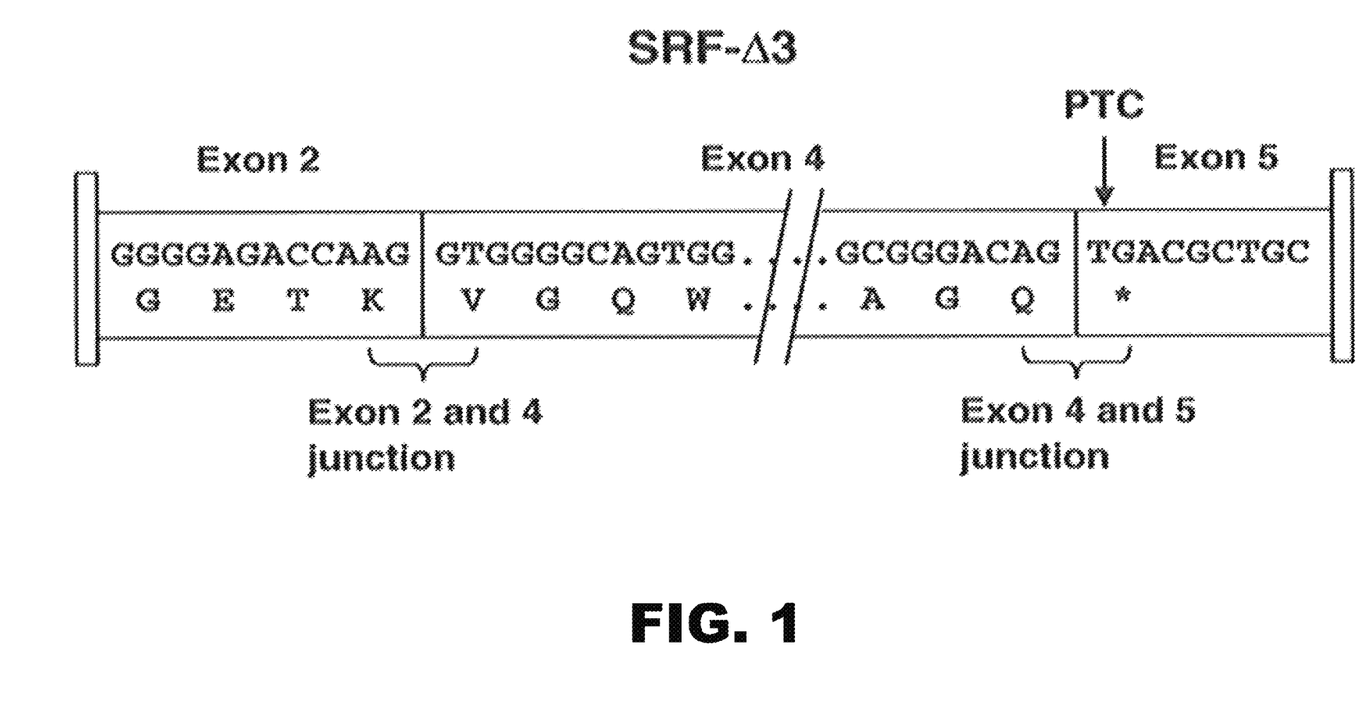
FIG. 1 depicts SEQ ID NO: 2 and SEQ ID NO: 3, which are a schematic representation of exon-exon junctions in SRFΔ3 showing exon2/exon4 junction and a premature termination codon (PTC) resulting from a shift in reading frame at exon 4.
Figure 2:
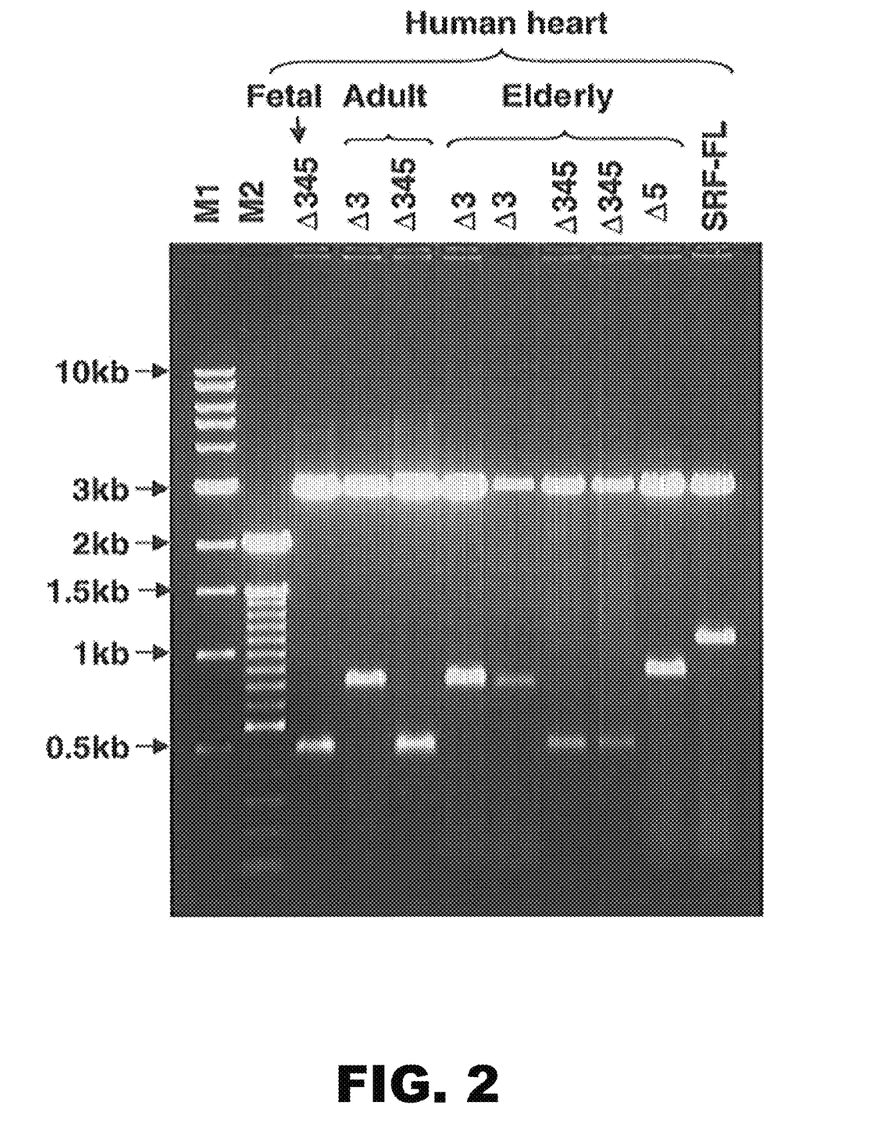
FIG. 2 depicts an agarose gel showing the presence of SRFΔ3 in human heart. Δ3 refers to SRFΔ3. Δ345 refers to SRFΔ345. Δ5 refers to SRFΔ5. SRF-FL refers to full-length SRF cDNA. M1 refers to the 1 kb DNA marker, M2 refers to the 100 bp DNA marker (New England Biolabs).

A total of six SRF transcripts were found in human tissues. They included a full-length SRF form and two of the previously identified isoforms, SRFΔ345 and SRFΔ5. SRF-FL was found in all age groups. Three novel SRF isoforms, SRFΔ3, SRFΔ34 and SRFΔ3456 were also identified (FIG. 1). The clones encoding isoform SRFΔ3, which lacks exon 3, were found in cDNA preparations from human cardiac and skeletal muscle (FIG. 2). Three out of the four new SRFΔ3 clones were found in cDNA preparations from very old hearts.

An increase of SRF isoforms with advancing age was observed in the human heart. The constitutive form of SRF (SRF-FL) and SRFΔ345 isoform (approximately 5%), was detected in the fetal heart. SRF-FL and two isoforms, SRFΔ345 (approximately 8%), and SRFΔ3 (approximately 4%), were detected in the young adult heart. SRF-FL and three isoform, SRFΔ345 (approximately 11%), SRFΔ3 (approximately 8%), and SRFΔ5 (less than 1%), were detected in the old adult heart. In addition, the expression of SRFΔ3 was increased in the heart of the old adult compared to that of the young adult individual. Even though SRFΔ5 was detected in the old adult heart, it was not detected in the young adult heart or fetal heart samples that were tested. These data suggest that the expression of the alternatively spliced SRF isoforms likely increase in old age. The human skeletal muscle was used as comparison. In human skeletal muscle, SRF-FL, SRFΔ345 and SRFΔ3, were observed.

Example 2

SRFΔ3 Protein Expression

Figure 3:
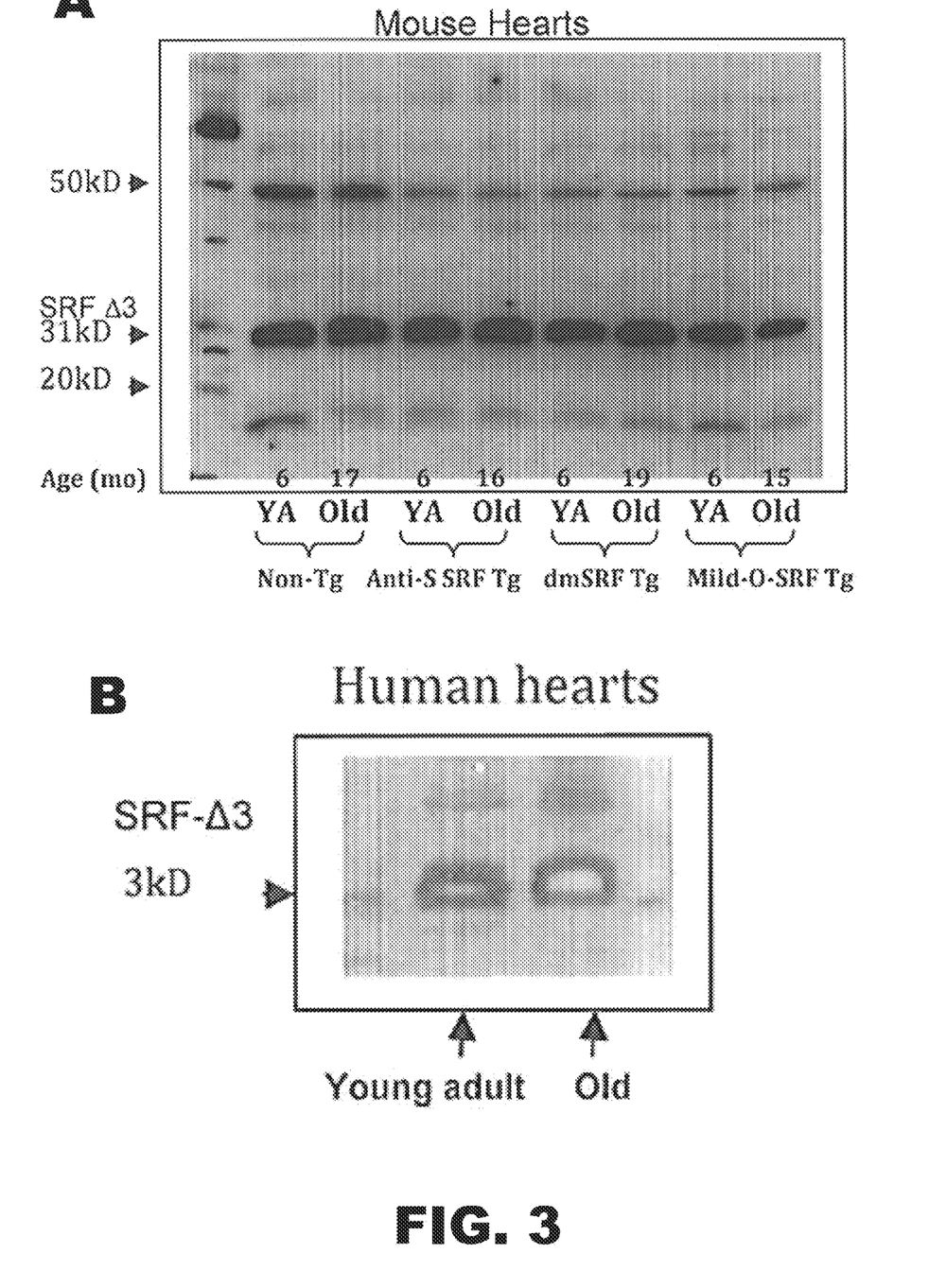
FIG. 3 depicts two Western blots showing that SRFΔ3 protein is present in mouse and human hearts. (A) Representative Western blot of mouse left ventricular tissues from 6 mo young (YA) and old (16-19 mo) mouse hearts of non-transgenic and various SRF transgenic mice. Anti-S SRF Tg=antisense SRF Tg mice with reduced expression of wild-type SRF. dmSRF Tg=SRF TG with over-expression of a mutant SRF. SRF protein, with reduced SRF protein expression in the heart. Mild-O-SRF Tg transgenic mice with mild over-expression of wild-type SRF protein in the heart. (B) Representative Western blot of human left ventricular tissues from young adult (30 yrs) old (70+ yrs) hearts.

An anti-SRFΔ3 antibody was developed. The antibody was raised against a 40-amino acid residue fragment corresponding to exon 4, unique to SRFΔ3 (FIG. 1). Using this antibody, Western blotting was able to detect the presence of the 31 kD SRFΔ3 protein in both mouse and human heart tissue (FIGS. 3A and B). Interestingly, expression of the SRFΔ3 isoform is increased in hearts of old vs. young adult rodents and humans.

Example 3

SRFΔ3 as an Anti-Proliferative Agent

Figure 4:
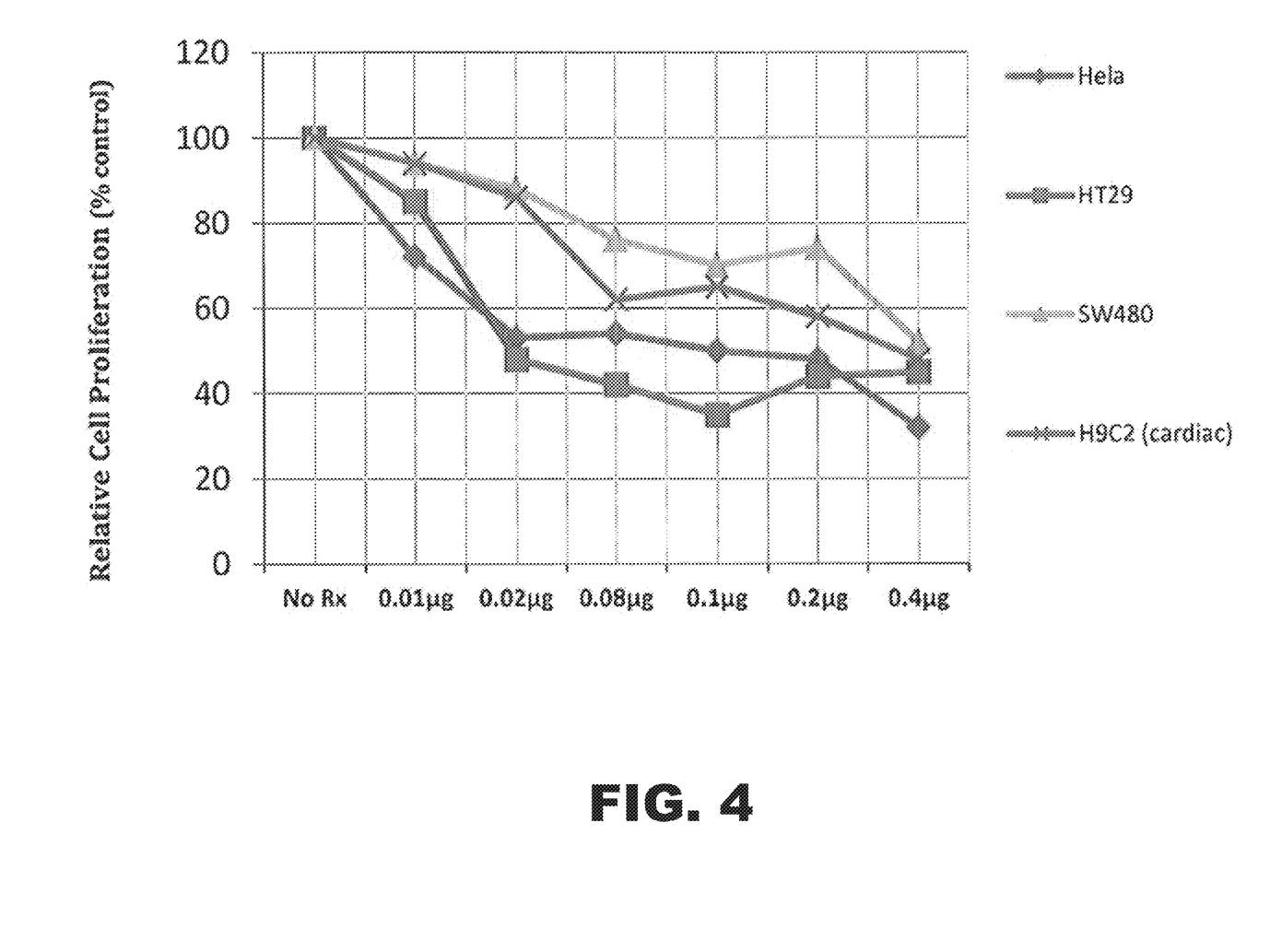
FIG. 4 graphically depicts effect of SRFΔ3 on proliferation of Hela cells, cancer cell lines HT29 and SW480 and the cardiomyocyte cell line H9C2 using MTS cell proliferation assays. In all proliferation assays, SRFΔ3 reduced cell proliferative activity. No Rx=no treatment. All experiments were performed in duplicate and repeated 3 times.

Plasmid pCDNA3.1-SRFΔ3 encoding SRFΔ3 was constructed. pCDNA3.1-SRFΔ3 was transfected into various cell lines and cell growth was measured using MTS cell proliferation assays. Expression of SRFΔ3 had a significant antiproliferative effect on 4 different cell lines (FIG. 4), including the HT29 and SW480 colon cancer lines and the H9C2 cardiogenic cell line, which has features of both cardiac and skeletal muscle. The H9C2 cells are derived from embryonic skeletal muscle and have sarcomeres, but are non-contractile.

Apart from its potential use as an anti-cancer therapy agent, SRFΔ3 might also be of potential use in other non-cancerous disease states with pathological proliferation such as cardiac hypertrophic conditions, proliferative kidney diseases, liver cirrhosis, cystic fibrosis, all conditions which are associated with severe morbidity and mortality.

Example 4

Figure 5:
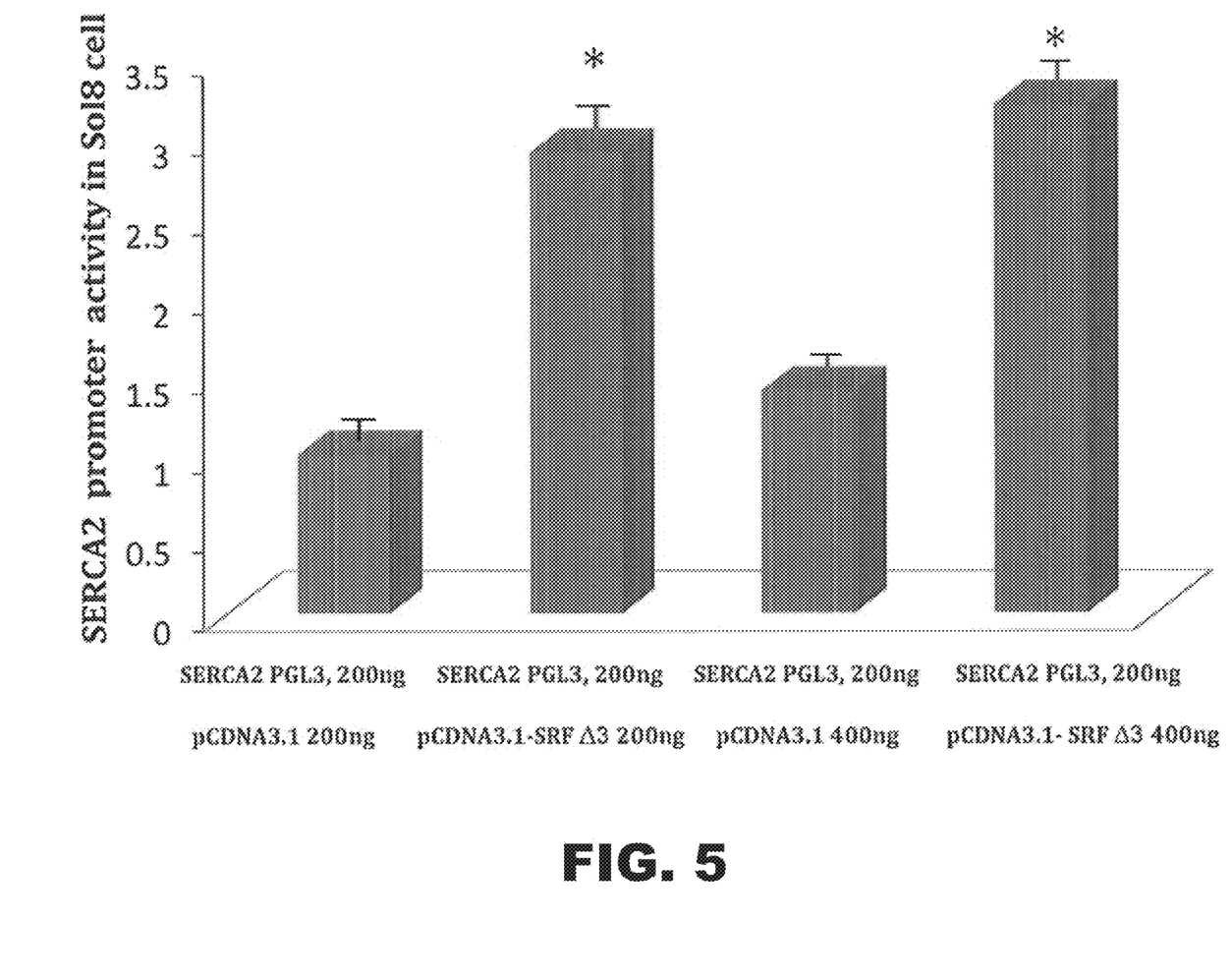
FIG. 5 depicts a plot showing the effect of SRFΔ3 on SERCA2 promoter activity in Sol8 cells. The cells were grown in DMEM with 10% bovine serum to reach a 90% confluence and co-transfected with 200 ng or 400 ng SRFΔ3-pcDNA3.1 and SERCA 2 PGL3 plasmid. SERCA2 promoter activity was determined using luciferase expression. All experiments were performed in triplicate and repeated at least 2 times.

Administration of SRFΔ3 in Cardiac and Skeletal Muscle Cells Increases SERCA2 Expression Transfection of pCDNA3.1-SRFΔ3 into Sol8 cells, a skeletal muscle cell line derived from normal mouse soleus leg muscles, to express SRFΔ3 resulted in a significant increase in SERCA2 promoter activity level (FIG. 5). Increase in SERCA2 expression was also observed in H9C2 cells, a cardiogenic cell line. SERCA2 activity is of key importance in normal cardiac and skeletal muscle function, maintenance, contractility and hypertrophy. Normal aging causes a reduction in SERCA2 expression in the old cardiac and skeletal muscle that is associated with progressive weakness of both and in the very old, the development of heart failure.

Hence SRFΔ3 may be of potential importance in the prevention and amelioration of congestive heart failure. It may also be of importance in the prevention of frailty and weakness of the skeletal muscle in the elderly. SRFΔ3 may also be of importance in primary skeletal muscle myopathy and atrophy and chronic muscle wasting syndromes with cachexia, such as in congestive heart failure, renal failure, COPD, cancer, HIV and other chronic infections.

Example 5

Other Effects of SRFΔ3 Administration

Figure 6:
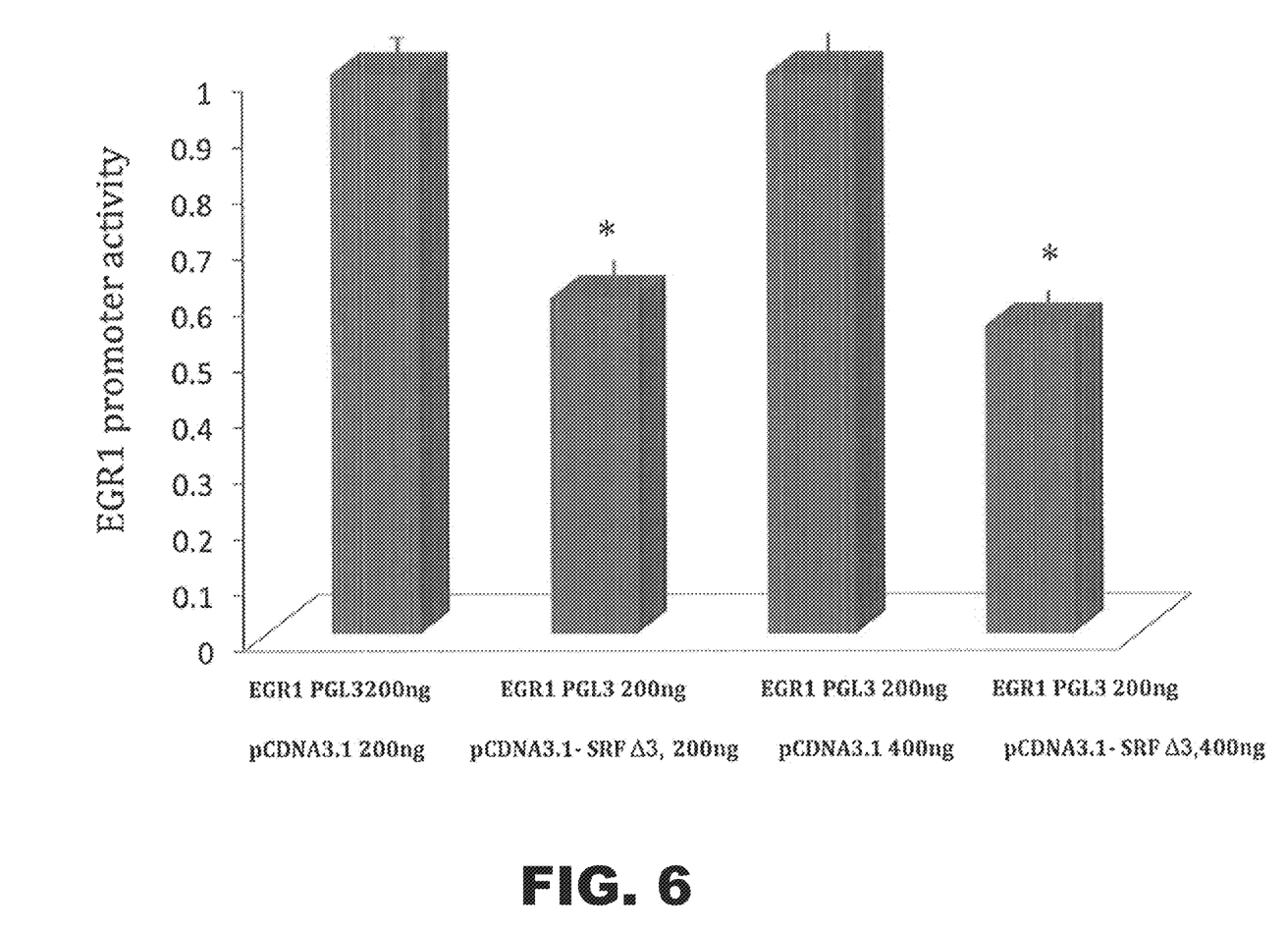
FIG. 6 depicts a plot showing the effect of SRFΔ3 on EGR1 promoter activity in NIH3T3 cells. NIH3T3 cells were grown in DMEM with 10% bovine serum to reach a 90% confluence. The cells were then co-transfected with SRFΔ3-pcDNA3.1 in 200 ng or 400 ng concentration and EGR1 PGL3 plasmid in 200 ng concentration. EGR1 promoter activity was determined with luciferase expression. All experiments were performed in triplicate and repeated at least 2 times.
Figure 7:
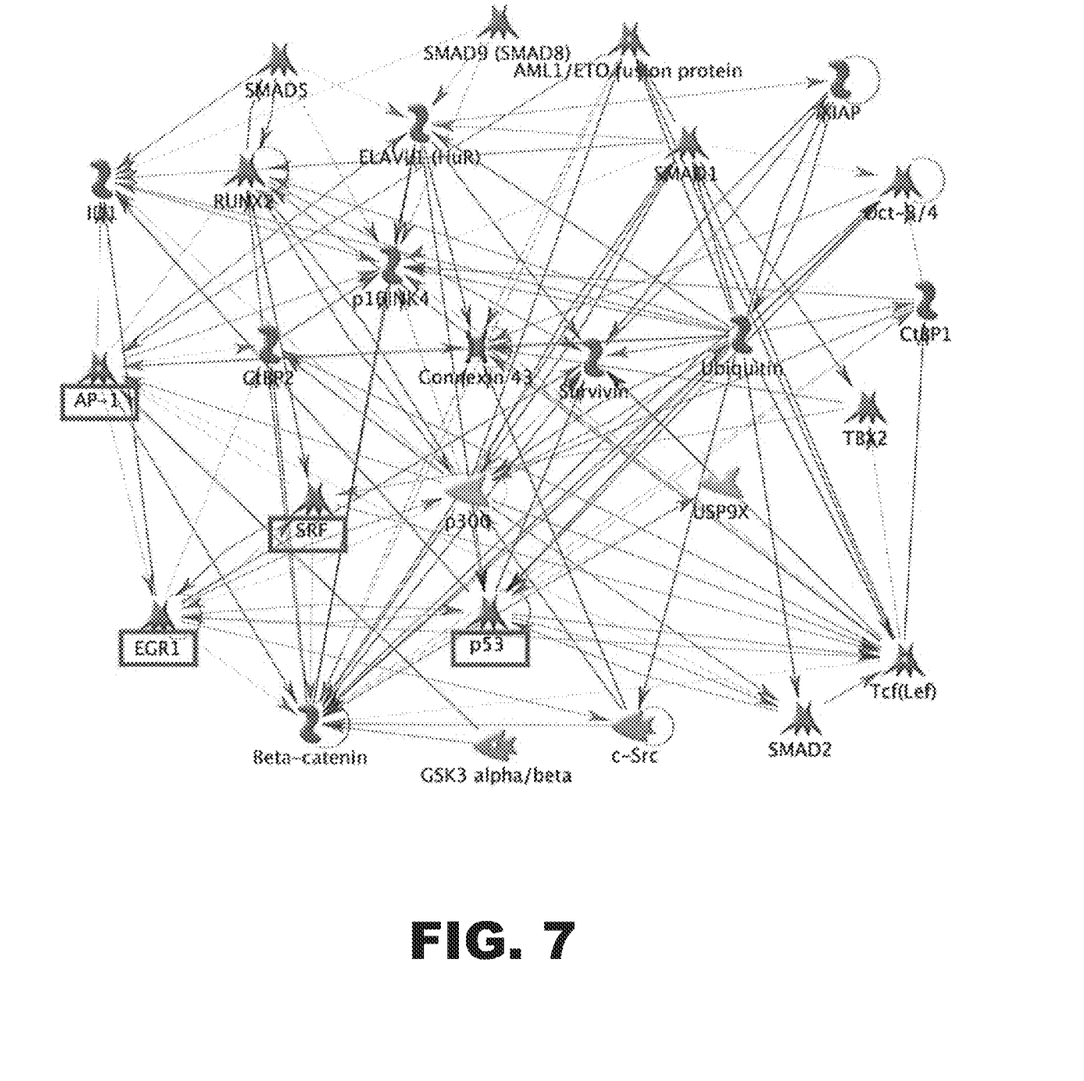
FIG. 7 depicts a diagram representing a GeneGo map highlighting some of the network connections of SRF and EGR-1 with transcriptions factors as p53, API and others.

SRFΔ3 significantly reduced the expression of the early growth response gene, EGR1, in NIH3T3 cells (FIG. 6). EGR1 is an important immediate early gene with rapid activation following stress, associated with increases in inflammatory cytokines and procoagulants. The EGR1 gene has also been implicated in prostate cancer, breast cancer, lung cancer and connective tissue diseases such as scleroderma and schizophrenia (FIG. 7).

Potential applications of EGR1 gene inhibition with SRFΔ3 may include therapy for prostate, breast and lung cancer as well as reduction of fibrotic diseases such as scleroderma, but also pathological fibrosis after myocardial infarction and tissue damage in various organs following ischemia or inflammatory injury.

Example 6

Cardiac-Specific Genes and Pathways Involved in Expression of SRF

Figure 8:
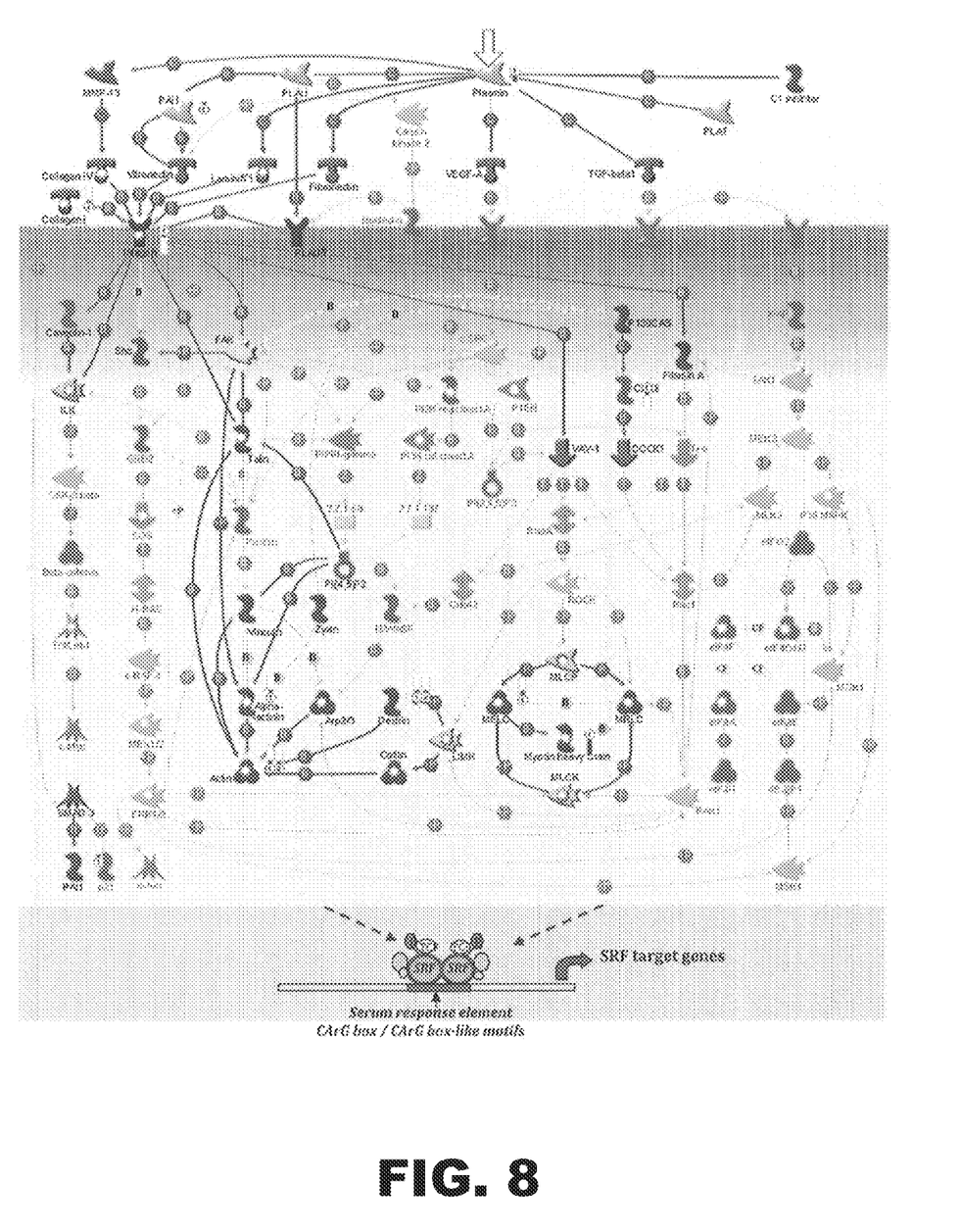

Serum response factor (SRF) is a member of the MADS family of transcription factors that regulates a number of immediate-early genes and muscle-specific genes, and regulates cell proliferation, cell size, and cell survival. SRF regulates target genes by binding to serum response elements (SREs), which contain a consensus CC(A/T)GGG (CArG) motif. This cognate binding site of SRF is found in the promoter region of certain immediate-early genes such as c-fos, and a number of muscle specific genes such as cardiac α-actin (FIG. 8).

What is claimed is:

1. A method of reducing proliferation of a cell in vitro, the method comprising: (a) administering an exogenous nucleic acid sequence encoding SRFΔ3 protein to a mammalian cell in cell culture, wherein in the nucleic acid, exons 2 and 4 of SRFΔ3 are joined, resulting in a frame shift in the translational reading frame at exon 4, and a premature termination codon in exon 5; and (b) performing a proliferation assay using the cell in (a); wherein a reduced proliferation rate of the treated cell in (a) compared to an untreated cell indicates effective inhibition of proliferation.

2. The method of claim 1, wherein the cell is a tumor cell line.

3. The method of claim 2, wherein the cell is a cell line is selected from the group consisting of HeLa, HT29, SW480 and H9C2.

4. The method of claim 1, wherein the nucleic acid sequence capable of expressing SRFΔ3 protein comprises SEQ ID NO: 1.

5. The method of claim 1, wherein the proliferation rate of the treated cell is reduced by about 80% to about 40% of the proliferation rate of an untreated cell.

6. The method of claim 1, wherein the proliferation rate of the treated cell is reduced by about 60% to about 20% of the proliferation rate of an untreated cell.

* * * * *